United States Patent
Sels et al.

(10) Patent No.: US 9,862,700 B2
(45) Date of Patent: Jan. 9, 2018

(54) PROCESS FOR PREPARING CYCLIC ESTERS AND CYCLIC AMIDES

(71) Applicant: Total Research & Technology Feluy, Seneffe (Feluy) (BE)

(72) Inventors: Bert Sels, Balen (BE); Michiel Dusselier, Kessel-Lo (BE)

(73) Assignee: TOTAL RESEARCH & TECHNOLOGY FELUY, Seneffe (BE)

( * ) Notice: Subject to any disclaimer, the term of this patent is extended or adjusted under 35 U.S.C. 154(b) by 0 days.

(21) Appl. No.: 15/399,189

(22) Filed: Jan. 5, 2017

(65) Prior Publication Data

US 2017/0114036 A1 Apr. 27, 2017

Related U.S. Application Data

(62) Division of application No. 14/765,703, filed as application No. PCT/EP2014/052493 on Feb. 7, 2014, now Pat. No. 9,573,924.

(30) Foreign Application Priority Data

Feb. 8, 2013 (EP) .................................. 13154707

(51) Int. Cl.
| | | |
|---|---|---|
| *C07D 241/08* | (2006.01) | |
| *C07D 319/12* | (2006.01) | |
| *C07D 313/04* | (2006.01) | |
| *C07D 223/08* | (2006.01) | |
| *C07D 223/10* | (2006.01) | |

(52) U.S. Cl.
CPC ......... *C07D 319/12* (2013.01); *C07D 223/08* (2013.01); *C07D 223/10* (2013.01); *C07D 313/04* (2013.01)

(58) Field of Classification Search
CPC ..................................................... C07D 241/08
See application file for complete search history.

(56) References Cited

U.S. PATENT DOCUMENTS

2010/0256398 A1* 10/2010 Pinkos ................. C07D 313/04
549/266

* cited by examiner

*Primary Examiner* — Bruck Kifle
(74) *Attorney, Agent, or Firm* — Albert Shung (57) ABSTRACT

The invention relates to a process for preparing a cyclic ester or a cyclic amide, comprising the step of:
contacting at least one hydroxycarboxylic acid and/or at least one amino-carboxylic acid; or an ester, or salt thereof; wherein said hydroxycarboxylic acid is a 2-hydroxycarboxylic acid, or a 6-hydroxycarboxylic acid; and wherein said amino carboxylic acid is a 2-amino-carboxylic acid or a 6-amino-carboxylic acid;
with at least one acidic zeolite comprising:
two or three interconnected and non-parallel channel systems, wherein at least one of said channel systems comprises 10-or more-membered ring channels; and a framework $Si/X_2$ ratio of at least 24 as measured by NMR; or
three interconnected and non-parallel channel systems, wherein at least two of said channel systems comprise 10-or more-membered ring channels; and a framework $Si/X_2$ ratio of at least 6 as measured by NMR;
wherein each X is Al or B, and wherein the process is performed at a pressure between 0.5 and 20 bar.

10 Claims, 4 Drawing Sheets

PROCESS FOR PREPARING CYCLIC ESTERS AND CYCLIC AMIDES

CROSS-REFERENCE TO RELATED APPLICATIONS

This application is a divisional of U.S. patent application Ser. No. 14/765,703, filed Aug. 4, 2015, which claims the benefit of PCT/EP2014/052493, filed Feb. 7, 2014, which claims priority from EP 13154707.7, filed Feb. 8, 2013.

FIELD OF THE INVENTION

The invention relates to a process for preparing cyclic esters and cyclic amides, which may be used as starting products for the preparation of polymers such as biopolymers.

BACKGROUND OF THE INVENTION

Cyclic esters are useful compounds that can be polymerized into polymeric materials. Such polymeric materials are useful in the preparation of biodegradable plastic materials and other plastic materials. Cyclic esters are also useful as plasticizers and as intermediates for production of surface-active agents and plasticizers.

Cyclic esters are usually prepared by condensing hydroxy acids to an oligomeric prepolymer. The prepolymer is then depolymerized to a cyclic ester. The production of a cyclic ester from an oligomeric prepolymer is sometimes referred to as a back-biting reaction. The back-biting reaction is typically a slow one, and a batch operation which extends over significant time and which results in undesirable byproducts. Extensive purification processes are therefore required to obtain cyclic esters of requisite purity.

Therefore, there remains a need for processes for preparing cyclic esters that overcome one or more of the aforementioned issues. It is an object of the present invention to provide a process for preparing cyclic esters and cyclic amides.

SUMMARY OF THE INVENTION

The present inventors have now surprisingly found that one or more of these objects can be obtained by the process of the present invention.

The present invention concerns a process for preparing a cyclic ester or a cyclic amide, comprising the step of contacting at least one hydroxycarboxylic acid and/or at least one amino-carboxylic acid; or an ester, or salt thereof; wherein said hydroxycarboxylic acid is a 2-hydroxycarboxylic acid or a 6-hydroxycarboxylic acid, and wherein said amino carboxylic acid is a 2-amino-carboxylic acid or a 6-amino-carboxylic acid;
  with at least one acidic zeolite, wherein said zeolite comprises:
    two or three interconnected and non-parallel channel systems wherein at least one of said channel systems comprises 10-or more-membered ring channels; and a framework $Si/X_2$ ratio of at least 24 as measured by NMR; or
    three interconnected and non-parallel channel systems wherein at least two of said channel systems comprise 10-or more-membered ring channels, and a framework $Si/X_2$ ratio of at least 6 as measured by NMR;
  wherein each X is Al or B.

Preferably, the invention relates to a process for preparing a cyclic ester or a cyclic amide, comprising the step of:
  contacting at least one hydroxycarboxylic acid and/or at least one amino-carboxylic acid; or an ester, or salt thereof; wherein said hydroxycarboxylic acid is a 2-hydroxycarboxylic acid, or a 6-hydroxycarboxylic acid; and wherein said amino carboxylic acid is a 2-amino-carboxylic acid or a 6-amino-carboxylic acid;
    with at least one acidic zeolite comprising:
      two or three interconnected and non-parallel channel systems, wherein at least one of said channel systems comprises 10-or more-membered ring channels; and a framework $Si/X_2$ ratio of at least 24 as measured by NMR; or
      three interconnected and non-parallel channel systems, wherein at least two of said channel systems comprise 10-or more-membered ring channels; and a framework $Si/X_2$ ratio of at least 6 as measured by NMR;
    wherein each X is Al or B, and wherein the process is performed at a pressure between 0.5 and 20 bar.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, which illustrates, by way of example, the principles of the invention.

BRIEF DESCRIPTION OF THE DRAWINGS

The following description of the figures of specific embodiments of the invention is merely exemplary in nature and is not intended to limit the present teachings, their application or uses. Throughout the drawings, corresponding reference numerals indicate like or corresponding parts and features.

FIG. 2 A, B: Graph plotting the rate of lactide production per acid site per hour and per gram zeolite per hour, respectively, for ZSM-5 and H-BEA zeolites with varying $Si/Al_2$ ratios.

DETAILED DESCRIPTION OF THE INVENTION

When describing the processes of the invention, the terms used are to be construed in accordance with the following definitions, unless a context dictates otherwise.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The recitation of numerical ranges by endpoints includes all numbers and fractions subsumed within the respective ranges, as well as the recited endpoints.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

All documents cited in the present specification are hereby incorporated by reference in their entirety.

The present process for preparing a cyclic ester or a cyclic amide, comprises the step of contacting at least one hydroxycarboxylic acid and/or at least one amino-carboxylic acid; or an ester, or salt thereof; as defined herein; with at least one acidic zeolite as defined herein.

Preferably, the present process for preparing a cyclic ester or a cyclic amide, comprises the step of contacting at least one hydroxycarboxylic acid and/or at least one amino-carboxylic acid; or an ester, or salt thereof; as defined herein; with at least one acidic zeolite as defined herein, and the process is performed at a pressure between 0.5 and 20 bar.

The term "zeolite" as used herein refers to both natural and synthetic microporous crystalline aluminosilicate materials having a definite crystalline structure as determined by X-ray diffraction. A zeolite comprises a system of channels which may be interconnected with other channel systems or cavities such as side-pockets or cages. The channel systems may be three-dimensional, two-dimensional or one-dimensional. A zeolite comprises $SiO_4$ and $XO_4$ tetrahedra, wherein X is Al (aluminium) or B (boron). A zeolite may comprise a combination of $AlO_4$ and $BO_4$ tetrahedra. In a preferred embodiment. X is Al, and the zeolite comprises no $BO_4$ tetrahedra. The $SiO_4$ and $XO_4$ tetrahedra are linked at their corners via a common oxygen atom. The Atlas of Zeolite Framework Types (C Baerlocher, L B McCusker, D H Olson, $6^{th}$ ed. Elsevier. Amsterdam, 2007) in conjunction with the web-based version (http://www.iza-structure.org/databases/) is a compendium of topological and structural details about zeolite frameworks, including the types of ring structures present in the zeolite and the dimensions of the channels defined by each ring type. Proven recipes and good laboratory practice for the synthesis of zeolites can be found in the "Verified synthesis of zeolitic materials" $2^{nd}$ Edition 2001.

Various proven recipes for the synthesis comprising $BO_4$ tetrahedra are available. For example, the synthesis and characterization of boron-based zeolites having a MFI topology has been described by Cichocki and Parasiewicz-Kaczmarska (Zeolites 1990, 10, 577-582).

Suitable zeolites for use in the present process typically comprise:
  at least two, preferably two or three, interconnected and non-parallel channel systems wherein at least one of said channel systems comprises 10-or more-membered ring channels; and a framework $Si/X_2$ ratio of at least 24 as measured by NMR; or
  three interconnected and non-parallel channel systems wherein at least two of said channel systems comprise 10-or more-membered ring channels, and a framework $Si/X_2$ ratio of at least 6 as measured by NMR;
  wherein each X is Al or B.

As used herein, the term "channel system" refers to a system of parallel and crystallographically equivalent channels, wherein the channels are 8-membered ring channels or larger, for example wherein the channels are 10-membered ring channels or 12-membered ring channels. Accordingly, as used herein, the term "channel" refers to an 8-or more-membered ring channel which is part of a system of parallel and crystallographically equivalent channels.

Suitable zeolites for use in the present process comprise 10-or more-membered ring channels, such as 10-membered ring channels (10MR), 12-membered ring channels (12MR), or larger. The ring size for each known zeolite framework type is provided in the Atlas of Zeolite Framework Types (C Baerlocher, L B McCusker, D H Olson, $6^{th}$ ed. Elsevier, Amsterdam, 2007), which is incorporated herein by reference.

As used herein the terms "8-membered ring channels" or "8MR" refer to a channel comprising unobstructed 8-membered rings, wherein the 8-membered rings define the smallest diameter of the channel. An 8-membered ring comprises 8 T atoms, and 8 alternating oxygen atoms (forming the ring), wherein each T is Si, Al or B. As used herein the terms "10-membered ring channels" or "10MR" refers to a channel comprising unobstructed 10-membered rings, wherein the 10-membered rings define the smallest diameter of the channel. A 10-membered ring comprises 10 T atoms, and 10 alternating oxygen atoms (forming the ring), wherein each T is Si, Al or B. As used herein the terms "12-membered ring channels" or "12MR" refers to a channel comprising unobstructed 12-membered rings, wherein the 12-membered rings define the smallest diameter of the channel. A 12-membered ring comprises 12 T atoms, and 12 alternating oxygen atoms (forming the ring), wherein each T is Si, Al or B. As used herein, the term "10-or-more-membered ring channel" refers to a 10-membered ring channel or larger, and therefore comprises for example both 10-membered ring channels and 12-membered ring channels.

The framework $Si/X_2$ ratio may be determined via Nuclear Magnetic Resonance (NMR) measurements, more particularly $^{29}Si$ and $^{27}Al$ NMR. In a preferred embodiment, there is no framework B, and the $Si/X_2$ ratio is equal to the $Si/Al_2$ ratio. The determination of the $Si/Al_2$ ratio by NMR may be performed as described by Klinowski (Ann. Rev. Mater Sci. 1988, 18, 189-218); or as described by G. Engelhardt and D. Michel (*High-Resolution Solid-State NMR of Silicates and Zeolites*. John Wiley & Sons, Chichester 1987. xiv, 485 pp). The determination of the $Si/B_2$ ratio by NMR may be performed as discussed by D. Trong On et al. (*Studies in Surface Science and Catalysis* 1995, 97, 535-541; *Journal of Catalysis*, November 1995, Volume 157, Issue 1, Pages 235-243).

The present inventors have found that, by using certain zeolites as catalysts, cyclic ester synthesis or cyclic amide synthesis can be simplified significantly. The present inventors have found that the use of zeolites as defined herein allow for the production of cyclic esters such as lactide in a single step, thus avoiding the condensation to a prepolymer and depolymerization towards cyclic ester. Moreover, the inventors found that zeolites as defined herein provide an excellent selectivity to the cyclic ester. Additionally, in contrast with the condensation-depolymerization process, no significant racemization occurs when using zeolites as a catalyst, thus avoiding the extensive purification. Zeolites are heterogeneous catalysts, and are therefore easy to separate from the product after reaction, in contrast with classic homogeneous catalysts such as sulfuric acid.

The present process comprises the step of contacting at least one hydroxycarboxylic acid and/or at least one aminocarboxylic acid; or an ester, or salt thereof, with at least one acidic zeolite, wherein said zeolite comprises:

at least two, preferably two or three, interconnected and non-parallel channel systems, wherein at least one of the channel systems comprises 10-or more-membered ring channels; and a framework $Si/X_2$ ratio of at least 24 as measured by NMR; or three interconnected and non-parallel channel systems wherein at least two of the channel systems comprise 10-or more-membered ring channels; and a framework $Si/X_2$ ratio of at least 6 as measured by NMR, wherein each X is Al or B.

and wherein said hydroxycarboxylic acid is a 2-hydroxycarboxylic acid or a 6-hydroxycarboxylic acid, and wherein said amino carboxylic acid is g2-amino-carboxylic acid or a 6-amino-carboxylic acid, preferably wherein "channel system" refers to a system of parallel and crystallographically equivalent channels, wherein the channels are 8-membered ring channels or larger.

Indeed, the inventors have found that the selectivity towards cyclic esters or amides highly depends on the zeolite architecture. It was found that the best results were obtained using zeolites comprising at least two interconnected and non-parallel channel systems (a 2D or 3D micropore geometry). Accordingly, the zeolites used in the process described herein comprise a 2D or 3D micropore geometry, more particularly an interconnected 2D or 3D micropore geometry.

Furthermore, zeolites suitable for the process described herein have channels which are large enough to accommodate the catalysis of the reaction from hydroxycarboxylic acid molecules to the respective cyclic ester. The inventors found that the best results were obtained with zeolites comprising at least one 10-or more-membered ring channel.

The present inventors have further found that the $Si/X_2$ ratio in the zeolite framework significantly influences the suitability of the zeolites for catalyzing the reaction of hydroxycarboxylic acids to cyclic esters.

Accordingly, in particular embodiments, the zeolite(s) for use in the process described herein may comprise a framework $Si/X_2$ ratio of at least 24, for example a framework $Si/Al_2$ ratio of at least 24, wherein the zeolite further comprises at least two interconnected and non-parallel channel systems wherein at least one of the interconnected and non-parallel channel systems comprises 10-or more-membered ring channels, i.e. at least one of the channel systems comprises 10-or more-membered ring channels, and at least one other channel system comprises 8-or more-membered ring channels. Examples of such zeolites are zeolites comprising a topology selected from the group comprising FER, MFI, and MWW.

In yet further embodiments, both of the at least two channel systems comprise 10-or more-membered ring channels. In particular embodiments, at least one of the channel systems comprises 12-or more-membered ring channels.

In certain embodiments, the zeolite for use in the process described herein may comprise a framework $Si/X_2$ ratio of at least 6, for example a framework $Si/Al_2$ ratio of at least 6: wherein the zeolite further comprises three interconnected and non-parallel channel systems wherein at least two of the interconnected and non-parallel channel systems comprise 10-or more-membered ring channels, i.e. at least two of the channel systems comprise 10-or more-membered ring channels, and the other channel system comprises 8-or more-membered ring channels. Examples of such zeolites include, but are not limited to zeolites comprising a topology selected from the group comprising BEA, FAU, and MEL.

In yet further embodiments, the three channel systems all comprise 10-or more-membered ring channels. In particular embodiments, at least one of the channel systems comprises 12-or more-membered channels. In certain embodiments, at least two of the channel systems comprise 12-or more-membered ring channels. Examples of such zeolites include, but are not limited to zeolites comprising a topology selected from the group comprising BEA and FAU.

In particular embodiments, the zeolite comprises at least two interconnected and non-parallel channel systems wherein at least one of the interconnected and non-parallel channel systems comprises 10-or more-membered ring channels; wherein the zeolite further comprises a framework $Si/X_2$ ratio of at least 24, more particularly of at least 25, for example a ratio of at least 30, for example a ratio of at least 35, for example a ratio of at least 40, for example a ratio of at least 50, for example a ratio of at least 60, for example a ratio of at least 70, for example a ratio of at least 80, for example a ratio of at least 90, for example or at least 100. Preferably, the zeolite comprises two or three interconnected and non-parallel channel systems wherein at least one of the interconnected and non-parallel channel systems comprises 10-or more-membered ring channels; wherein the zeolite further comprises a framework $Si/Al_2$ ratio of at least 24, more particularly a ratio of at least 25, for example a ratio of at least 30, for example a ratio of at least 35, for example a ratio of at least 40, for example a ratio of at least 50, for example a ratio of at least 60, for example a ratio of at least 70, for example a ratio of at least 80, for example a ratio of at least 90, or for example a ratio of at least 100.

In particular embodiments, the zeolite comprises three interconnected and non-parallel channel systems wherein at least two of the interconnected and non-parallel channel systems comprise 10-or more-membered ring channels; wherein the zeolite further comprises a framework $Si/X_2$ ratio of at least 6, more particularly at least 8, for example a ratio of at least 10, for example a ratio of at least 15, for example a ratio of at least 20, for example a ratio of at least 25, for example a ratio of at least 30, for example a ratio of at least 35, for example a ratio of at least 40, for example a ratio of at least 50, for example a ratio of at least 60, for example a ratio of at least 70, for example a ratio of at least 80, for example a ratio of at least 90, or for example a ratio of at least 100. Preferably, the zeolite comprises three interconnected and non-parallel channel systems wherein at least two of the interconnected and non-parallel channel systems comprise 10-or more-membered ring channels; wherein the zeolite further comprises a framework $Si/Al_2$ ratio of at least 6, more particularly of at least 8, for example a ratio of at least 10, for example a ratio of at least 15, for example a ratio of at least 20, for example a ratio of at least 25, for example a ratio of at least 30, for example a ratio of at least 35, for example a ratio of at least 40, for example a ratio of at least 50, for example a ratio of at least 60, for example a ratio of at least 70, for example a ratio of at least 80, for example a ratio of at least 90, or for example a ratio of at least 100.

In most embodiments, the conversion of hydroxycarboxylic acids and/or aminocarboxylic acids to cyclic esters or cyclic amides increases as the $Si/X_2$ ratio increases, preferably as the $Si/Al_2$ ratio increases. In some embodiments, it is observed that at high $Si/X_2$ ratios, the conversion may decrease as the $Si/X_2$ ratio increases further. Without wishing to be bound by theory, this is believed to be related to the low amount of acid sites in zeolites with high $Si/X_2$ ratio. Therefore, in particular embodiments, the zeolite has a framework $Si/X_2$ ratio below 280. In further embodiments, the zeolite has a framework $Si/X_2$ ratio below 200. Preferably, the zeolite has a framework $Si/Al_2$ ratio below 280. In further embodiments, the zeolite has a framework $Si/Al_2$ ratio below 200.

The zeolites used in the process described herein may comprise $AlO_4$ tetrahedra, $BO_4$ tetrahedra, or both. Accordingly, in some embodiments. $X_2$ is $(Al_2+B_2)$. Thus, for a given zeolite, the $Si/X_2$ framework ratio remains the same upon substitution of framework Al by B, or vice versa. However, it is envisaged that in particular embodiments, the zeolites may not comprise $BO_4$ tetrahedra, or an insignificant amount thereof (e.g. an Al/B ratio of 100 or more). Thus, in particular embodiments, $X_2$ may be $Al_2$.

The $Si/X_2$ ratios referred to herein are molar ratios as determined via NMR, unless specified otherwise. It will be understood by the skilled person that the $Si/X_2$ ratio referred to herein is equal to the $SiO_2/X_2O_3$ molar ratio, wherein $X_2O_3$ is ($Al_2O_3$ and/or $B_2O_3$). Moreover, the skilled person will understand that by dividing the $Si/X_2$ ratio by two, the $Si/X$ molar ratio is obtained, wherein X is (Al and/or B).

Preferably, the channels defined by the zeolite topology are large enough to be accessible for the monomers, but small enough to prevent significant formation and/or diffusion of timers or higher order oligomers. Accordingly, in particular embodiments, the zeolite only comprises channels with a ring size of at most 18, preferably of at most 14, for example of at most 12.

In a preferred embodiment, suitable zeolites for use in the process described herein comprises a topology selected from the group comprising BEA, MFI, FAU, MEL, FER, and MWW. The inventors have found that these zeolites provide a particularly high selectivity towards cyclic esters. In certain embodiments, the zeolite(s) comprise a topology selected from the group consisting of BEA, MFI, FAU, and MWW. In specific embodiments, the zeolite(s) comprise a zeolite with a BEA topology.

Exemplary commercially available zeolites suitable for use in the processes described herein include, but are not limited to, Beta polymorph A (BEA topology), ZSM-5 (Mobil; MFI topology), Y zeolite (FAU topology), and MCM-22 (Mobil; MWW topology).

In certain embodiments, the zeolite comprises channels having an average (equivalent) diameter of at least 4.5 Å. More particularly, the zeolite may comprise two or more non-parallel channels having an average diameter of at least 4.5 Å. The channel diameter may be determined theoretically via knowledge of the zeolite framework type, or via x-ray diffraction (XRD) measurements, as will be known by the skilled person. Preferably, the zeolite comprises two or more non-parallel and interconnected channels having an average (equivalent) diameter between 4.5 and 13.0 Å, more preferably between 4.5 and 8.5 Å. Preferably, the diameter for the appropriate topology is obtained from international standard literature: the Atlas of Zeolite structures or the corresponding online database, found at http://www.iza-structure.org/databases/, as referenced above. The (equivalent) diameter of the channels may also be determined experimentally via $N_2$ adsorption, for example as discussed by Groen et al. (*Microporous and Mesoporous Materials* 2003, 60, 1-17), Storck et al. (*Applied Catalysis A: General* 1998, 174, 137-146) and Rouquerol et al. (Rouquerol F, Rouquerol J and Sing K. *Absorption by powders and porous solids: principles, methodology and applications*, Academic Press, London, 1999).

In some embodiments, the zeolite may further comprise mesopores. The presence of mesopores may increase the accessibility of the hydroxycarboxylic acids to the micropores, and may therefore further increase the reaction speed. However, it is also envisaged that the zeolite may not comprise mesopores.

As used herein the term "mesopores" refers to pores in the zeolite crystal having average diameters of 2.0 nm to 50 nm. For pore shapes deviating from the cylinder, the above ranges of diameter of mesopores refer to equivalent cylindrical pores. The mesopore average diameter may be determined by gas sorption techniques such as $N_2$ adsorption.

The zeolite(s) may be used as such, for example as a powder. In certain embodiments, the zeolite(s) may be formulated into a catalyst by combining with other materials that provide additional hardness or catalytic activity to the finished catalyst product. Materials which can be blended with the zeolite may be various inert or catalytically active materials, or various binder materials. These materials include compositions such as kaolin and other clays, phosphates, alumina or alumina sol, titania, metal oxide such as zirconia, quartz, silica or silica sol, metal silicates, and mixtures thereof. These components are effective in densifying the catalyst and increasing the strength of the formulated catalyst. Various forms of rare earth metals can also be added to the catalyst formulation. The catalyst may be formulated into pellets, spheres, extruded into other shapes, or formed into spray-dried particles. The amount of zeolite which is contained in the final catalyst product may range from 0.5 to 99.9 weight %, preferably from 2.5 to 99.5 weight % of the total catalyst, preferably from 2.5 to 95 weight %, preferably from 2.5 to 90 weight % of the total catalyst, most preferably from 2.5 to 80 weight %; for example from 20 to 95 weight %, preferably from 20 to 90 weight %, most preferably from 20 to 80 weight %, with weight % based on the total weight of catalyst product.

In some embodiments, the zeolite(s) for use in the processes described herein can be exposed to a (post-synthesis) treatment to increase the $Si/X_2$ framework ratio. Methods to increase the $Si/Al_2$ ratio of zeolites are known in the art, and include dealumination of the framework via (hydro)thermal treatment, extraction of framework aluminum with acid, and replacement of framework aluminum with silicon by reaction with silicon halides or hexafluorosilicates. An exemplary method of dealumination is described by Remy et al. (*J. Phys. Chem.* 1996, 100, 12440-12447; hereby incorporated by reference).

The zeolites for use in the process described herein preferably are Brønsted acidic zeolites, i.e. having proton donating sites in the micropores. In some embodiments, the zeolite has a Brønsted acid density between 0.05 and 6.5 mmol/g dry weight. When all Al T-sites are counterbalanced with an acidic proton (as opposed to a cation), the Brønsted acid density can be directly derived from the Si/Al$_2$ ratio, for example as discussed in the Handbook of Heterogeneous Catalysis, second edition, edited by G. Ertl, H. Knözinger, F. Schüth and J. Weitkamp, Wiley 2008.

The zeolites for use in the processes described herein can be obtained in acidic form (acidic H-form zeolite) or (partly) exchanged with a cation other than H$^+$. In some embodiments, the acidic H-form zeolites can be used as such. In some other embodiments, the zeolites for use in the processes described herein can be exposed to a (post-synthesis) treatment to increase the Brønsted acid density. Brønsted acid sites in zeolites can be readily generated by aqueous ion exchange with an ammonium salt, followed by thermal decomposition of the ammonium ions inside the zeolite. Alternatively, the acid sites may be generated by aqueous ion exchange with the salt of a multivalent metal cation (such as Mg$^{2+}$, Ca$^{2+}$, La$^{3+}$, or mixed rare-earth cations), followed by thermal dehydration (J. Weitkamp, *Solid State Ionics* 2000, 131, 175-188; hereby incorporated by reference).

In contrast with polymeric catalysts (e.g. Amberlyst™), the zeolite catalysts described herein may be regenerated and reused in the process. Accordingly, particular embodiments of the process described herein may comprise a step of regenerating the zeolite catalyst. Regeneration of the zeolite catalysts can be performed via washing or calcination. Preferably, regeneration of the zeolite catalysts is done via calcination, for example at a temperature of at least 150° C. In particular embodiments, the calcination temperature is at least 200° C., for example at least 300° C., for example at least 400° C., for example about 450° C.

In the processes described herein, at least one hydroxycarboxylic acid, and/or at least one aminocarboxylic acid are used as starting material.

The hydroxycarboxylic acid used in the context of the processes described herein is selected from a 2-hydroxycarboxylic acid or a 6-hydroxycarboxylic acid. Also salts, or esters of such compounds may be used. In particular embodiments, only one hydroxycarboxylic acid is used in the process. In some embodiments, it is envisaged that two different hydroxycarboxylic acids can be used, for example for the preparation of asymmetric dimeric cyclic esters. In particular embodiments, said 2-hydroxycarboxylic acid comprises at least 3 carbon atoms.

In some embodiments, the zeolite is contacted with at least one compound of formula (I)

(I)

or a salt, or ester thereof;
wherein
R$^5$ is OH or NH$_2$; and
R$^1$ and R$^2$ are each independently hydrogen or a group selected from C$_{1-6}$alkyl; C$_{2-6}$alkenyl; C$_{6-10}$aryl; C$_{1-10}$alkylC$_{6-10}$arylene; C$_{6-10}$arylC$_{1-6}$alkylene; or C$_{2-5}$alkynyl; each group being optionally substituted by one or more substituents selected from C$_{1-6}$ alkyl, C$_{1-6}$alkyloxy. In further embodiments, R$^1$ and R$^2$ are each independently selected from hydrogen or a group selected from C$_{1-4}$alkyl, C$_{2-4}$alkenyl, or C$_{2-4}$alkynyl; each group being optionally substituted by one or more substituents selected from C$_{1-6}$alkyl, C$_{1-6}$alkyloxy; preferably R$^1$ and R$^2$ are each independently selected from hydrogen, C$_{1-6}$alkyl, C$_{2-6}$alkenyl, C$_{6-10}$aryl, C$_{1-10}$alkylC$_{6-10}$arylene, C$_{6-10}$arylC$_{1-6}$alkylene, or C$_{2-4}$alkynyl. In further embodiments, R$^1$ and R$^2$ are each independently selected from hydrogen, C$_{1-4}$alkyl, or C$_{2-4}$alkenyl.

In particular embodiments, at least one of R$^1$ and R$^2$ is not hydrogen. Unless expressly stated otherwise, each of the following terms has the indicated meaning:

The term "C$_{1-6}$alkyl", as a group or part of a group, refers to a hydrocarbyl radical of Formula C$_n$H$_{2n+1}$ wherein n is a number ranging from 1 to 6. Generally, the alkyl groups comprise from 1 to 6 carbon atoms, for example 1 to 4 carbon atoms. Alkyl groups may be linear, or branched and may be substituted as indicated herein. When a subscript is used herein following a carbon atom, the subscript refers to the number of carbon atoms that the named group may contain. Thus, for example, C$_{1-4}$alkyl means an alkyl of 1 to 4 carbon atoms. Examples of alkyl groups are methyl, ethyl, propyl, isopropyl, butyl, isobutyl, sec-butyl, tert-butyl, pentyl and its chain isomers, hexyl and its chain isomers.

The term "C$_{2-6}$alkenyl" by itself or as part of another substituent, refers to an unsaturated hydrocarbyl group, which may be linear, or branched, comprising one or more carbon-carbon double bonds. Preferred alkenyl groups thus comprise between 2 and 6 carbon atoms, preferably between 2 and 4 carbon atoms. Non-limiting examples of C$_{2-6}$alkenyl groups include ethenyl, 2-propenyl, 2-butenyl, 3-butenyl, 2-pentenyl and its chain isomers, 2-hexenyl and its chain isomers, 2-4-pentadienyl and the like.

The term "C$_{2-6}$alkenyl" by itself or as part of another substituent, refers to an unsaturated hydrocarbyl group, which may be linear, or branched, comprising one or more carbon-carbon triple bonds. Preferred alkynyl groups thus comprise between 2 and 6 carbon atoms, preferably between 2 and 4 carbon atoms. Non limiting examples of C$_{2-6}$alkynyl groups include ethynyl, 2-propynyl, 2-butynyl, 3-butynyl, 2-pentynyl and its chain isomers, 2-hexynyl and its chain isomers and the like.

As used herein, the term "C$_{6-10}$aryl", by itself or as part of another substituent, refers to a polyunsaturated, aromatic hydrocarbyl group having a single ring (i.e. phenyl) or multiple aromatic rings fused together (e.g. naphthalene), or linked covalently, typically containing 6 to 10 atoms; wherein at least one ring is aromatic. Examples of C$_{6-10}$aryl include phenyl, naphthyl, indanyl, or 1,2,3,4-tetrahydronaphthyl.

The term "C$_{1-6}$alkoxy" or "C$_{1-6}$alkyloxy" as used herein refers to a radical having the Formula —OR$^d$ wherein R$^d$ is C$_{1-6}$alkyl. Non-limiting examples of suitable alkoxy include methoxy, ethoxy, propoxy, isopropoxy, butoxy, isobutoxy, sec-butoxy, tert-butoxy, pentyloxy and hexyloxy.

As used herein, the term "C$_{1-6}$alkylene", by itself or as part of another substituent, refers to C$_{1-6}$alkyl groups that are divalent, i.e., with two single bonds for attachment to two other groups. Alkylene groups may be linear or branched and may be substituted as indicated herein. Non-limiting examples of alkylene groups include methylene (—CH$_2$—), ethylene (—CH$_2$—CH$_2$—), methylmethylene (—CH(CH$_3$)—), 1-methyl-ethylene (—CH(CH$_3$)—CH$_2$—), n-propylene (—CH$_2$—CH$_2$—CH$_2$—), 2-methylpropylene (—CH$_2$—CH(CH$_3$)—CH$_2$—), 3-methylpropylene (—CH$_2$—CH$_2$—CH(CH$_3$)—), n-butylene (—CH$_2$—CH$_2$—

$CH_2$—$CH_2$—), 2-methylbutylene (—$CH_2$—$CH(CH_3)$—$CH_2$—$CH_2$—), 4-methylbutylene (—$CH_2$—$CH_2$—$CH_2$—$CH(CH_3)$—), pentylene and its chain isomers, hexylene and its chain isomers.

The term "$C_{6-10}$aryl$C_{1-6}$alkylene", as a group or part of a group, means a $C_{1-6}$alkyl as defined herein, wherein a hydrogen atom is replaced by a $C_{6-10}$aryl as defined herein. Examples of $C_{6-10}$aryl$C_{1-6}$alkyl radicals include benzyl, phenethyl, dibenzylmethyl, methylphenylmethyl, 3-(2-naphthyl)-butyl, and the like.

As used herein, the term "$C_{1-6}$alkyl$C_{6-10}$arylene", by itself or as part of another substituent, refers to a $C_{6-10}$aryl group as defined herein, wherein a hydrogen atom is replaced by a $C_{1-6}$alkyl as defined herein.

In some embodiments, the hydroxycarboxylic acid is a 2-hydroxycarboxylic acid, more particularly a compound of formula (Ia)

(Ia)

or a salt, or ester thereof;
wherein $R^1$ and $R^2$ are each independently hydrogen or a group selected from $C_{1-6}$alkyl; $C_{2-6}$alkenyl; $C_{6-10}$aryl; $C_{1-10}$alkyl$C_{6-10}$arylene; $C_{6-10}$aryl$C_{1-6}$alkylene; or $C_{2-6}$alkynyl; each group being optionally substituted by one or more substituents selected from $C_{1-6}$alkyl, $C_{1-6}$alkyloxy. In further embodiments, $R^1$ and $R^2$ are each independently selected from hydrogen; or a group selected from $C_{1-4}$alkyl, $C_{2-4}$alkenyl, or $C_{2-4}$alkynyl; each group being optionally substituted by one or more substituents selected from $C_{1-6}$alkyl, $C_{1-6}$alkyloxy; preferably $R^1$ and $R^2$ are each independently selected from hydrogen, $C_{1-6}$alkyl, $C_{2-6}$alkenyl, $C_{6-10}$aryl, $C_{1-10}$alkyl$C_{6-10}$arylene, $C_{6-10}$aryl$C_{1-6}$alkylene, or $C_{2-6}$alkynyl. In further embodiments, $R^1$ and $R^2$ are each independently selected from hydrogen, $C_{1-4}$alkyl, or $C_{2-4}$alkenyl.

In certain embodiments, at least one of $R^1$ and $R^2$ is not hydrogen.

In certain embodiments, the 2-hydroxycarboxylic acid (also referred to as "α-hydroxycarboxylic acid") is a compound of formula (Ia), wherein $R^1$ is hydrogen and $R^2$ is a group selected from $C_{1-6}$alkyl; $C_{2-6}$alkenyl; $C_{6-10}$aryl; $C_{1-10}$alkyl$C_{6-10}$arylene; $C_{6-10}$aryl$C_{1-6}$alkylene; or $C_{2-6}$alkynyl; each group being optionally substituted by one or more substituents selected from $C_{1-6}$alkyl, $C_{1-6}$alkyloxy; preferably $R^2$ is selected from $C_{1-6}$alkyl; $C_{2-6}$alkenyl; or $C_{2-6}$alkynyl; preferably $R^2$ is $C_{1-4}$alkyl, or $C_{2-4}$alkenyl.

In preferred embodiments, the compound of formula (I) or (Ia) can be selected from the group comprising lactic acid, 2-hydroxybutanoic acid, 2-hydroxy-3-butenoic acid, and 2-hydroxyhexanoic acid. Preferably the compound of formula (I) or (Ia) is lactic acid.

In some embodiments, the hydroxycarboxylic acid is a 6-hydroxycarboxylic acid, for example 6-hydroxyhexanoic acid, optionally substituted with one or more groups selected from the group consisting of halo, $C_{1-4}$alkyl, $C_{2-4}$alkenyl, or $C_{2-4}$alkynyl. 6-hydroxycarboxylic acids are particularly useful for the preparation of ε-lactones, such as caprolactone.

Preferably, said hydroxycarboxylic acid is selected from the group comprising lactic acid, 2-hydroxybutanoic acid, 2-hydroxy-3-butenoic acid, 2-hydroxyhexanoic acid, 6-hydroxyhexanoic acid, and glycolic acid. Preferably, said hydroxycarboxylic acid is lactic acid.

In some embodiments, the aminocarboxylic acid is a 2-aminocarboxylic acid, more particularly a compound of formula (Ib)

(Ib)

or a salt, or ester thereof;
wherein $R^1$ and $R^2$ are each independently hydrogen or a group selected from $C_{1-6}$alkyl; $C_{2-6}$alkenyl; $C_{6-10}$aryl; $C_{1-10}$alkyl$C_{6-10}$arylene; $C_{6-10}$aryl$C_{1-6}$alkylene; or $C_{2-6}$alkynyl; each group being optionally substituted by one or more substituents selected from $C_{1-6}$alkyl, $C_{1-6}$alkyloxy. In further embodiments, $R^1$ and $R^2$ are each independently selected from hydrogen or a group selected from $C_{1-4}$alkyl, $C_{2-4}$alkenyl, or $C_{2-4}$alkynyl; each group being optionally substituted by one or more substituents selected from $C_{1-4}$alkyl, $C_{1-6}$alkyloxy; preferably $R^1$ and $R^2$ are each independently selected from hydrogen, $C_{1-6}$alkyl, $C_{2-6}$alkenyl, $C_{6-10}$aryl, $C_{1-10}$alkyl$C_{6-10}$arylene, $C_{6-10}$aryl$C_{1-6}$alkylene, or $C_{2-6}$alkynyl. In further embodiments, $R^1$ and $R^2$ are each independently selected from hydrogen, $C_{1-4}$alkyl, or $C_{2-4}$alkenyl.

In certain embodiments, at least one of $R^1$ and $R^2$ is not hydrogen.

In certain embodiments, the aminocarboxylic acid is a compound of formula (Ib), wherein $R^1$ is hydrogen and $R^2$ is a group selected from $C_{1-6}$alkyl; $C_{2-6}$alkenyl; $C_{6-10}$aryl; $C_{1-10}$alkyl$C_{6-10}$arylene; $C_{6-10}$aryl$C_{1-6}$alkylene; or $C_{2-6}$alkynyl; each group being optionally substituted by one or more substituents selected from $C_{1-6}$alkyl, $C_{1-6}$alkyloxy; preferably $R^2$ is selected from $C_{1-6}$alkyl; $C_{2-6}$alkenyl; or $C_{2-6}$alkynyl; preferably $R^2$ is $C_{1-4}$alkyl, or $C_{2-4}$alkenyl.

In preferred embodiments, the compound of formula (I) or (Ib) can be alanine.

In some embodiments, the aminocarboxylic acid is a 6-aminocarboxylic acid, for example 6-aminohexanoic acid, optionally substituted with one or more groups selected from the group consisting of halo, $C_{1-4}$alkyl, $C_{2-4}$alkenyl, or $C_{2-4}$alkynyl. 6-aminocarboxylic acids are particularly useful for the preparation of caprolactam and derivatives thereof.

The processes described herein may be used for the production of various cyclic esters, or cyclic amides, such as dimeric cyclic esters, lactones, dimeric cyclic amides, or lactams.

In preferred embodiments, the cyclic ester or cyclic amide prepared by the process described herein, is a compound of formula (II):

(II)

wherein
$Z^1$ is O or NH;
$Z^2$ is O or NH;

$R^1$ and $R^2$ are each independently hydrogen or a group selected from $C_{1-6}$alkyl; $C_{2-6}$alkenyl; $C_{6-10}$aryl; $C_{1-10}$alkyl$C_{6-10}$arylene; $C_{6-10}$aryl$C_{1-6}$alkylene; or $C_{2-6}$alkynyl; each group being optionally substituted by one or more substituents selected from $C_{1-6}$alkyl, $C_{1-6}$alkyloxy. In further embodiments, $R^1$ and $R^2$ are each independently selected from hydrogen or a group selected from $C_{1-4}$alkyl, $C_{2-4}$alkenyl, or $C_{2-4}$alkynyl; each group being optionally substituted by one or more substituents selected from $C_{1-6}$alkyl, $C_{1-6}$alkyloxy; preferably $R^1$ and $R^2$ are each independently selected from hydrogen, $C_{1-6}$alkyl, $C_{2-6}$alkenyl, $C_{6-10}$aryl, $C_{1-10}$alkyl$C_{6-10}$arylene, $C_{6-10}$aryl$C_{1-6}$alkylene, or $C_{2-6}$alkynyl. In further embodiments, $R^1$ and $R^2$ are each independently selected from hydrogen, $C_{1-4}$alkyl, or $C_{2-4}$alkenyl.

In certain embodiments, at least one of $R^1$ and $R^2$ is not hydrogen.

Compounds of formula (II) may be obtained by reaction of one or more compounds of formula (I) as described herein.

In preferred embodiments, the cyclic ester or cyclic amide prepared by the processes described herein is symmetric.

In some embodiments, it is also envisaged that the dimeric cyclic ester or cyclic amide may be asymmetric. For the preparation of asymmetric compounds of formula (II), two different compounds of formula (I) are required.

Preferably, the present process, comprises the step of contacting at least one compound of formula (I), a salt or an ester thereof,
with at least one acidic zeolite thereby obtaining a compound of formula (II),
wherein said zeolite comprises:
at least two interconnected and non-parallel channel systems wherein at least one of the channel systems comprises 10-or more-membered ring channels; and a framework $Si/X_2$ ratio of at least 24 as measured by NMR; or
three interconnected and non-parallel channel systems wherein at least two of the channel systems comprise 10-or more-membered ring channels; and a framework SIX, ratio of at least 6 as measured by NMR;
wherein each X is Al or B.

Preferably, the present process, comprises the step of contacting at least one compound of formula (I), a salt or an ester thereof,
with at least one acidic zeolite thereby obtaining a compound of formula (II),
wherein said zeolite comprises:
two or three interconnected and non-parallel channel systems wherein at least one of the channel systems comprises 10-or more-membered ring channels; and a framework $Si/Al_2$ ratio of at least 24 as measured by NMR; or
three interconnected and non-parallel channel systems wherein at least two of the channel systems comprise 10-or more-membered ring channels; and a framework $Si/Al_2$ ratio of at least 6 as measured by NMR.

In preferred embodiments, the cyclic ester prepared by the process described herein, is a compound of formula (IIa):

(IIa)

wherein $R^1$ and $R^2$ are each independently hydrogen or a group selected from $C_{1-6}$alkyl; $C_{2-6}$alkenyl; $C_{6-10}$aryl; $C_{1-10}$alkyl$C_{6-10}$arylene; $C_{6-10}$aryl$C_{1-6}$alkylene; or $C_{2-6}$alkynyl; each group being optionally substituted by one or more substituents selected from $C_{1-6}$alkyl, $C_{1-6}$alkyloxy; and wherein at least one of $R^1$ and $R^2$ is not hydrogen. In further embodiments, $R^1$ and $R^2$ are each independently selected from hydrogen or a group selected from $C_{1-4}$alkyl, $C_{2-4}$alkenyl, or $C_{2-4}$alkynyl; each group being optionally substituted by one or more substituents selected from $C_{1-6}$alkyl, $C_{1-6}$alkyloxy; and wherein at least one of $R^1$ and $R^2$ is not hydrogen; preferably $R^1$ and $R^2$ are each independently selected from hydrogen, $C_{1-6}$alkyl, $C_{2-6}$alkenyl, $C_{6-10}$aryl, $C_{1-10}$alkyl$C_{6-10}$arylene, $C_{6-10}$aryl$C_{1-6}$alkylene, or $C_{2-6}$alkynyl; and wherein at least one of $R^1$ and $R^2$ is not hydrogen. In further embodiments, $R^1$ and $R^2$ are each independently selected from hydrogen, $C_{1-4}$alkyl, or $C_{2-4}$alkenyl, wherein at least one of $R^1$ and $R^2$ is not hydrogen.

Compounds of formula (IIa) may be obtained by reaction of one or more compounds of formula (Ia) as described herein.

In certain embodiments, the hydroxycarboxylic acid is a compound of formula (IIa), wherein $R^1$ is hydrogen and $R^2$ is a group selected from $C_{1-6}$alkyl; $C_{2-6}$alkenyl; $C_{6-10}$aryl; $C_{1-10}$alkyl$C_{6-10}$arylene; $C_{6-10}$aryl$C_{1-6}$alkylene; or $C_{2-6}$alkynyl; each group being optionally substituted by one or more substituents selected from $C_{1-6}$alkyl, $C_{1-6}$alkyloxy; preferably $R^2$ is selected from $C_{1-6}$alkyl; $C_{2-6}$alkenyl; or $C_{2-6}$alkynyl; preferably $R^2$ is $C_{1-4}$alkyl, or $C_{1-4}$alkenyl.

In preferred embodiments, the compound of form a (IIa) prepared by the processes described herein is symmetric.

In some embodiments, it is also envisaged that the compound of formula (IIa) may be asymmetric. For the preparation of asymmetric compounds of formula (IIa), two different compounds of formula (Ia) are required.

In some embodiments, the cyclic ester is a lactone, more particularly a ε-lactone, which may be prepared by using a 6-hydroxycarboxylic acid as hydroxyhexanoic acid.

Preferably, the process for preparing a cyclic ester, comprises the step of contacting at least one compound of formula (Ia), with at least one acidic zeolite thereby obtaining a compound of formula (IIa),
wherein said zeolite comprises:
at least two interconnected and non-parallel channel systems wherein at least one of the channel systems comprises 10-or more-membered ring channels; and a framework $Si/X_2$ ratio of at least 24 as measured by NMR; or
three interconnected and non-parallel channel systems wherein at least two of the channel systems comprise 10-or more-membered ring channels; and a framework $Si/X_2$ ratio of at least 6 as measured by NMR,
wherein each X is Al or B.

More preferably, the process for preparing a cyclic ester, comprises the step of contacting at least one compound of formula (Ia), with at least one acidic zeolite thereby obtaining a compound of formula (IIa),
wherein said zeolite comprises:
two or three interconnected and non-parallel channel systems wherein at least one of the channel systems comprises 10-or more-membered ring channels; and a framework $Si/Al_2$ ratio of at least 24 as measured by NMR; or
three interconnected and non-parallel channel systems wherein at least two of the channel systems comprise 10-or more-membered ring channels; and a framework $Si/Al_2$ ratio of at least 6 as measured by NMR.

In a preferred embodiment, lactic acid is used in the presence of at least one zeolite as defined herein to produce lactide. Preferably, L-lactic acid is used in the presence of at least one zeolite as defined herein to produce L-L-lactide. Preferably, D-lactic acid is used in the presence of at least one zeolite as defined herein to produce D-D-lactide.

In some embodiments, the cyclic amide prepared by the process described herein, is a compound of formula (IIb):

(IIb)

wherein $R^1$ and $R^2$ are each independently hydrogen or a group selected from $C_{1-6}$alkyl; $C_{2-6}$alkenyl; $C_{6-10}$aryl; $C_{1-10}$alkyl$C_{6-10}$arylene; $C_{6-10}$aryl$C_{1-6}$alkylene; or $C_{2-6}$alkynyl; each group being optionally substituted by one or more substituents selected from $C_{1-6}$alkyl, $C_{1-6}$alkyloxy. In further embodiments, $R^1$ and $R^2$ are each independently selected from hydrogen or a group selected from $C_{1-4}$alkyl, $C_{2-4}$alkenyl, or $C_{2-4}$alkynyl; each group being optionally substituted by one or more substituents selected from $C_{1-6}$alkyl, $C_{1-6}$alkyloxy; preferably $R^1$ and $R^2$ are each independently selected from hydrogen, $C_{1-6}$alkyl, $C_{2-6}$alkenyl, $C_{6-10}$aryl, $C_{1-10}$alkyl$C_{6-10}$arylene, $C_{6-10}$aryl$C_{1-6}$alkylene, or $C_{2-6}$alkynyl. In further embodiments, $R^1$ and $R^2$ are each independently selected from hydrogen, $C_{1-4}$alkyl, or $C_{2-4}$alkenyl.

In particular embodiments, at least one of $R^1$ and $R^2$ is not hydrogen.

Compounds of formula (IIb) may be obtained by reaction of one or more compounds of formula (Ib) as described herein.

In certain embodiments, the hydroxycarboxylic acid is a compound of formula (IIb), wherein $R^1$ is hydrogen and $R^2$ is a group selected from $C_{1-6}$alkyl; $C_{2-6}$alkenyl; $C_{6-10}$aryl; $C_{1-10}$alkyl$C_{6-10}$arylene; $C_{6-10}$aryl$C_{1-6}$alkylene; or $C_{2-6}$alkynyl; each group being optionally substituted by one or more substituents selected from $C_{1-6}$alkyl, $C_{1-6}$alkyloxy; preferably $R^2$ is selected from $C_{1-6}$alkyl; $C_{2-6}$alkenyl; or $C_{2-6}$alkynyl; preferably $R^2$ is $C_{1-4}$alkyl, or $C_{2-4}$alkenyl.

In preferred embodiments, the compound of formula (IIb) prepared by the processes described herein is symmetric.

In some embodiments, it is also envisaged that the compound of formula (IIb) may be asymmetric. For the preparation of asymmetric compounds of formula (IIb), two different compounds of formula (Ib) are required.

In some embodiments, the cyclic amide is a lactam, more particularly a ε-lactam, such as caprolactam, which may be prepared by using a 6-aminocarboxylic acid as aminohexanoic acid.

Preferably, the process for preparing a cyclic amide, comprises the step of contacting at least one compound of formula (Ib), with at least one acidic zeolite thereby obtaining a compound of formula (IIb),
wherein said zeolite comprises:
two or three interconnected and non-parallel channel systems wherein at least one of the channel systems comprises 10-or more-membered ring channels; and a framework Si/X$_2$ ratio of at least 24 as measured by NMR; or three interconnected and non-parallel channel systems wherein at least two of the channel systems comprise 10-or more-membered ring channels; and a framework Si/X$_2$ ratio of at least 6 as measured by NMR
wherein each X is Al or B.

The hydroxycarboxylic acid and/or aminocarboxylic acid is provided in no solution or emulsion, preferably in solution.

An appropriate solvent may be one in which the reaction products described herein are soluble and which has an appropriate boiling point. More particularly, the boiling point preferably is sufficiently high so that at the boiling point temperature an acceptable reaction rate is achieved, but sufficiently low such that the formation of degradation products can be avoided or minimized. Preferably, the solvent forms an azeotrope with water, thereby allowing the removal of water via azeotropic distillation. Azeotropic solvents can include water immiscible aromatic solvents, water immiscible aliphatic or cyclic hydrocarbon solvents, water soluble solvents, or mixtures thereof. Water immiscible azeotropic solvents are preferred because, after distillation, they can be readily separated with the solvent being recycled and the water being taken out of the system. Moreover, potential byproducts obtained during the reaction process (such as water soluble short oligomers of the hydroxycarboxylic acid and/or aminocarboxylic acid) will typically dissolve in the water phase, while the cyclic esters and/or cyclic amides of interest typically remain in the organic solvent phase. This may facilitate the separation of the byproducts from the products of interest via extraction, and subsequent re-entry of the water soluble products (after hydrolysis) in the reaction process.

Solvents which are not preferred because of being potentially reactive with cyclic esters include alcohols, organic acids, esters and ethers containing alcohol, peroxide and/or acid impurities, ketones and aldehydes with a stable enol form, and amines.

Suitable solvents may include aromatic hydrocarbon solvents such as benzene, toluene, xylene, ethylbenzene, trimethylbenzene (e.g. 1,3,5-trimethylbenzene), methylethylbenzene, n-propylbenzene, isopropylbenzene, diethylbenzene, isobutylbenzene, triethylbenzene, diisopropylbenzene, n-amylnaphthalene, and trimethylbenzene; ether solvents such as ethyl ether, isopropyl ether, n-butyl ether, n-hexyl ether, 2-ethylhexyl ether, ethylene oxide, 1,2-propylene oxide, dioxolane, 4-methyldioxolane, 1,4-dioxane, dimethyldioxane, ethylene glycol diethyl ether, ethylene glycol dibutyl ether, diethylene glycol diethyl ether, diethylene glycol di-n-butyl ether, tetrahydrofuran, and 2-methyltetrahydrofuran; aliphatic hydrocarbon solvents such as n-pentane, isopentane, n-hexane, isohexane, n-heptane, isoheptane, 2,2,4-trimethylpentane, n-octane, isooctane, cyclohexane, and methylcyclohexane; and ketone solvents such as acetone, methyl ethyl ketone, methyl n-propyl ketone, methyl n-butyl ketone, diethyl ketone, methyl isobutyl ketone, methyl n-pentyl ketone, ethyl n-butyl ketone, methyl n-hexyl ketone, diisobutyl ketone, trimethylnonanone, cyclohexanone, 2-hexanone, methylcyclohexanone, 2,4-pentanedione, acetonylacetone, acetophenone, and fenchone.

Particularly preferred solvents include, but are not limited to toluene, ortho-xylene, meta-xylene, para-xylene, ethylbenzene, propylbenzene, trimethylbenzene, anisol, or mixtures thereof.

In the processes as described herein, the hydroxycarboxylic acid(s) and/or aminocarboxylic acid(s) may be provided in a composition, such as in a solvent or diluent, which comprises the hydroxycarboxylic acid(s) and/or aminocarboxylic acid(s) in high concentrations, for example in concentrations of at least 1 weight % (wt %) based on the total weight of the composition, for example of at least 3 weight % (wt %) based on the total weight of the composition, for example of at least 5 weight % (wt %) based on the total weight of the composition, for example of at least 10 wt %, for example of at least 15 wt %, for example of at least 20 wt %, for example of at least 25 wt %, for example of at least 30 wt %, for example of at least 35 wt %, for example of at least 40 wt %, for example of at least 45 wt %, or for example of at least 50 wt % based on the total weight of the composition. In preferred embodiments, the hydroxycarboxylic acid (or salt, or ester thereof) may be provided in a composition comprising the hydroxycarboxylic acid (or salt, ester or amide thereof) in a concentration of at least 1 weight % based on the total weight of the composition. In further embodiments, the composition may comprise the hydroxycarboxylic acid, preferably lactic acid, in a concentration of at least 5 wt %, for example of at least 5 wt %, for example of at least 10 wt %, for example of at least 15 wt %, for example of at least 20 wt %, for example of at least 25 wt %, for example of at least 30 wt %, for example of at least 35 wt %, for example of at least 40 wt %, for example of at least 45 wt %, or for example of at least 50 wt % based on the total weight of the composition.

The process described herein is preferably performed under conditions of water removal. This may be obtained via a variety of methods, such as azeotropic distillation, evaporation, using molecular sieves or osmotic membranes, using anhydrous salts that form hydrated crystals with water, and contacting the feedstream with water absorptive materials such as polysaccharides or silica. Preferably azeotropic distillation is used. In preferred embodiments, the water is removed at least partially from the reaction mixture by azeotropic distillation, for example via a Dean-Stark apparatus.

The processes described herein may be performed at or near atmospheric pressure, and are typically performed at a pressure between 0.5 and 20 bar. In particular embodiments, the processes are performed at a pressure between 0.5 and 5 bar, more particularly between 0.9 and 1.1 bar.

The reaction may be performed at a relatively low temperature, and may therefore require less energy than other processes known in the art. In particular embodiments, the reaction is performed at the boiling point of the reaction mixture. In particular embodiments, the temperature of the heating device used for the reaction can be ranging from 50 to 300° C. In an embodiment, a higher temperature of the heating device will result in an increased reflux power at the same boiling temperature of the reaction mixture.

In particular embodiments, pure isomeric forms of the hydroxycarboxylic acid or aminocarboxylic acid can be used. However, it is also envisaged that in certain embodiments, a racemic mixture of the hydroxycarboxylic acid or aminocarboxylic acid can be used. Pure isomeric forms are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

The term "enantiomeric excess" or "% ee" as used herein refers to the amount of an enantiomer with respect to another. It can be calculated as follows:

$$\% \text{ ee} = [([A]-[B]):([A]+[B])] \times 100,$$

wherein [A] is the concentration of one of the enantiomers, and [B] is the concentration of the other enantiomer. The concentration of each of the enantiomers is, of course, expressed on the same basis, and can be expressed on either a weight of molar basis because the enantiomers have the same molecular weight.

Consequently, if a mixture of enantiomers is obtained during any of the following preparation methods, it can be separated by liquid chromatography using a suitable chiral stationary phase. Suitable chiral stationary phases are, for example, polysaccharides, in particular cellulose or amylose derivatives. Commercially available polysaccharide based chiral stationary phases are ChiralCel™ CA, OA, OB, OC, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like.

The processes described herein may be therefore be used for the preparation of enantiomerically pure cyclic esters. Indeed, the inventors found that during the process, no significant racemisation occurs. This means that if enantiomerically pure starting products (hydroxycarboxylic acids) are used, the resulting cyclic esters will also be enantiomerically pure, without further purification. Accordingly, in particular embodiments the hydroxycarboxylic acid(s) used in the processes described herein are enantiomerically pure, with an enantiomeric excess of at least 90%, preferably at least 95%.

Lactide has two asymmetric carbon atoms so it may be obtained in three stereoisomeric forms: L-L-lactide in which both asymmetric carbon atoms possess the L (or S) configuration; D-D-lactide in which both asymmetric carbon atoms possess the D (or R) configuration; and meso-lactide (D-L-lactide) in which one asymmetric carbon atom has the L-configuration and the other has the D-configuration.

In certain embodiments of the processes described herein, the hydroxycarboxylic acid is L-lactic acid (with an enantiomeric excess of at least 90%, preferably at least 95%, more preferably at least 98%) and the corresponding cyclic ester is L-L-lactide.

In certain embodiments of the processes described herein, the hydroxycarboxylic acid is D-lactic acid (with an enantiomeric excess of at least 90%, preferably of at least 95%, more preferably of at least 98%) and the corresponding cyclic ester is D-D-lactide.

The invention will now be illustrated by the following, non-limiting illustrations of particular embodiments of the invention.

EXAMPLES

Example 1: Preparation of Lactide from Lactic Acid

In this example several zeolites were tested as catalyst for the synthesis of L-L-lactide from L-lactic acid.

The following zeolites were used: CBV500, CBV600, CBV720, CBV760, and CBV780 (available from Zeolyst International, in NH$_4$ or H-form); H-BEA (available from Süd-Chemie). NH$_4$-ZSM-5 with various Si/Al$_2$ ratios (available from Zeolyst International); H-MOR (available from Süd-Chemie); H-FER (available from Zeolyst International), H-MCM-22 (available from ACSMaterial); LaX and LaY (made by starting from NaY or NaX, available from Evonik, according to C. F. Heylen and P. A. Jacobs, (Advances in Chemistry Series, 1973, 121, 490-500)).

The zeolites were used in their Brønsted acidic form (H-form). In general, when zeolites were provided (partly) exchanged with other cations (such as Sodium cations), they were exchanged and calcined to maximize the acidity and achieve the H-form. Typically, 100 mL of an aqueous solution of 0.5 M NH$_4$Cl was added per 1.0 gram of (e.g. Na) zeolite on wet basis. The mixture was heated for 4 hours under reflux conditions. Then, the zeolite was isolated by filtration and the exchange procedure was repeated. The zeolite was isolated again, and washed with 1 L of water. In this way, the NH$_4$-form of the zeolite is obtained. To transform this ammonium exchanged form into the Brønsted acidic form, the zeolite was typically calcined for 12 hours at a temperature of 450° C. A temperature ramp of 3° C./min was applied. The resulting zeolites were stored at room temperature in contact with air.

In a typical experiment, a reaction flask was loaded with a mixture of about 10 wt % L-lactic acid (L-LA) in toluene. Unless mentioned otherwise, the solution was prepared by mixing 1 g of 90 wt % L-LA (aqueous, obtained from Acros Organics) with 10 ml toluene. In one experiment (using the H-FER zeolite as catalyst), the solution was prepared by mixing 1.65 g of 50 wt % L-LA (aqueous, obtained from Sigma-Aldrich) with 10 ml toluene. In the conditions used for the experiments herein, no significant difference was observed between these starting solutions under these conditions.

Figure 1:
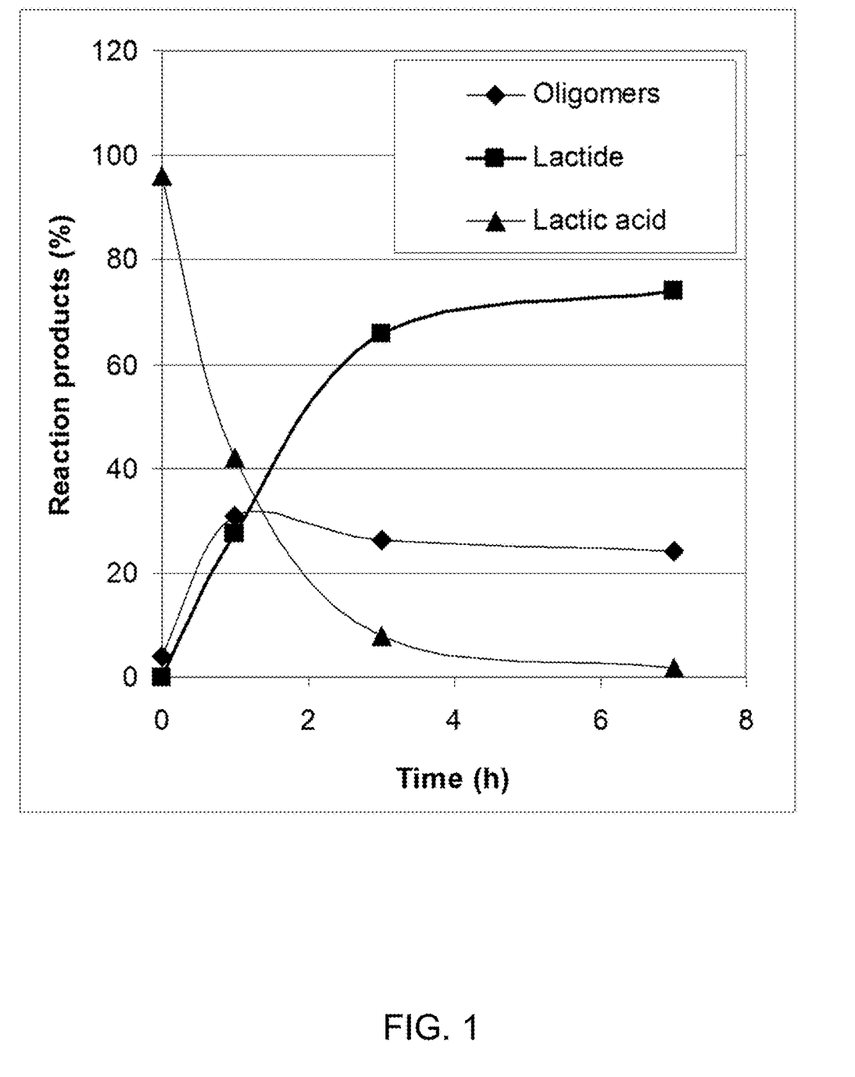
FIG. 1 Graph plotting the relative amount of lactic acid oligomers, lactide and lactic acid in a reactor at different times, using H-BEA zeolite catalyst with a $Si/Al_2$ ratio of 25.

The zeolite was added to the reaction mixture (about 0.5 g of zeolite per 10 mL solution), and the mixture was heated by placing the reaction flask in a hot oil bath at a temperature of about 130° C., and continuously mixed, the temperature of the reaction mixture was dependent on the used solvent and composition. A Dean-Stark trap was used for removal of water from the reaction mixture. Typically, the reaction mixture was heated for about 3 hours under stirring, after which the mixture was cooled to room temperature. The relative amounts of lactic acid oligomers, lactic acid, and lactide in the reaction mixture after 3 hours was indicative of the yield obtainable with each catalyst, as the reaction mixture typically does not change significantly after 3 hours for a good catalyst. This can be appreciated from FIG. 1, which shows the relative amount of reaction products in a reactor at different times, using a H-BEA zeolite catalyst with a Si/Al$_2$ ratio of 25. However, it is noted that for some catalysts, the maximal concentrations may be obtained faster.

Reference experiments were conducted using the known catalysts sulfuric acid (0.01 g per 10 mL solution) and Amberlyst® 15 Wet (about 0.5 g per 10 mL solution). The amount of reference catalysts is chosen such that the total amount of acid sites is similar to the amount of acid sites of the zeolites, thus allowing a fair comparison.

For each experiment, the total conversion rate of the lactic acid, and the lactide yield were determined via $^1$H NMR. Also control measurements using gas chromatography with flame ionization detector (GC/FID) and high-pressure liquid chromatography (HPLC) with uv-visible detector were performed. The total conversion of the lactic acid includes the fraction of lactic acid which had reacted to lactide, trimers, or other oligomers. The lactide yield only includes the fraction of fed lactic acid which has reacted to lactide.

All zeolites having two or three interconnected and non-parallel channel systems, with at least one of said systems comprising 10-or more-membered ring channels and a framework Si/Al$_2$ ratio of at least 24, and all zeolites having three interconnected and non-parallel channel systems, with at least two of said channel systems comprising 10-or more-membered ring channels and a framework Si/Al$_2$ ratio of at least 6, provided lactide yields above 20%, up to about 70%.

The results of the various experiments are summarized in Table 1. It is noted that for some zeolites, the framework Si/Al$_2$ ratio, may differ from the bulk Si/Al$_2$ ratio. For all zeolites, the framework Si/Al$_2$ ratio is provided, as this is most relevant ratio for the catalysis. For some zeolites, the bulk Si/Al$_2$ ratio is also provided (between brackets).

TABLE 1

| Catalyst Name | Topology | Ring size | Number of interconnected non parallel channel systems | Si/Al$_2$ framework ratio | LA conversion (%) | Lactide yield (%) |
|---|---|---|---|---|---|---|
| H-FER* | FER | 10-8 | two systems (with one system with 10-membered ring channels) | 25 | 78.0* | 25.1* |
| H-MCM-22 | MWW | 10-10 | two systems with 10-membered ring channels | 25 | 84.7 | 31.4 |
| LaY | FAU | 12-12-12 | three systems with 12-membered ring channels | 5.2 | 72.4 | 10.5 |
| LaX | FAU | 12-12-12 | three systems with 12-membered ring channels | 2.4 | 85.5 | 12 |
| H-MOR | MOR | 12-8 | Channel systems not interconnected (Parallel channel system with 12- and 8-membered rings) | 22 | 71.5 | 18.4 |

TABLE 1-continued

| Catalyst Name | Topology | Ring size | Number of interconnected non parallel channel systems | Si/Al$_2$ framework ratio | LA conversion (%) | Lactide yield (%) |
|---|---|---|---|---|---|---|
| H-BEA | BEA | 12-12-12 | three systems with 12-membered ring channels | 150 | 98.0 | 59.1 |
| H-BEA | BEA | 12-12-12 | three systems with 12-membered ring channels | 25 | 94.4 | 67.9 |
| HCBV 780 | FAU | 12-12-12 | three systems with 12-membered ring channels | 75 (74) | 93.3 | 45.7 |
| HCBV 760 | FAU | 12-12-12 | three systems with 12-membered ring channels | 60 (54.6) | 97.0 | 52.4 |
| HCBV 600 | FAU | 12-12-12 | three systems with 12-membered ring channels | 19 (5.6) | 89.9 | 53.4 |
| HCBV 500 | FAU | 12-12-12 | three systems with 12-membered ring channels | 9 (5.2) | 85.7 | 21.2 |
| H-ZSM 5 | MFI | 10-10 | two systems with 10-membered ring channels | 280 | 56.2 | 20.3 |
| H-ZSM 5 | MFI | 10-10 | two systems with 10-membered ring channels | 160 | 88.5 | 52.6 |
| H-ZSM 5 | MFI | 10-10 | two systems with 10-membered ring channels | 80 | 78.8 | 42.7 |
| H-ZSM 5 | MFI | 10-10 | two systems with 10-membered ring channels | 50 | 71.5 | 27.8 |
| H-ZSM 5 | MFI | 10-10 | two systems with 10-membered ring channels | 23 | 61.1 | 9.4 |
| H$_2$SO$_4$ | na | na | na | na | 100 | 8.1 |
| Amberlyst 15 | na | na | na | na | 94.4 | 20.2 |
| No catalyst | na | na | na | na | 52.1 | 8.1 | na: not applicable
*starting solution prepared by mixing 1.65 g of 50 wt % L-LA (aqueous) with 10 ml toluene From the amount of lactide obtained, the total (dry) weight of zeolite used, and the acid site density of the zeolite in each experiment, it is possible to calculate the rate of lactide formation per acid site for each zeolite. The acid site density can be estimated by assuming that each framework Al atom of the zeolite corresponds with an acid site. These estimated values generally correspond well with values for acidity as determined via pyridine sorption.

Figure 2:
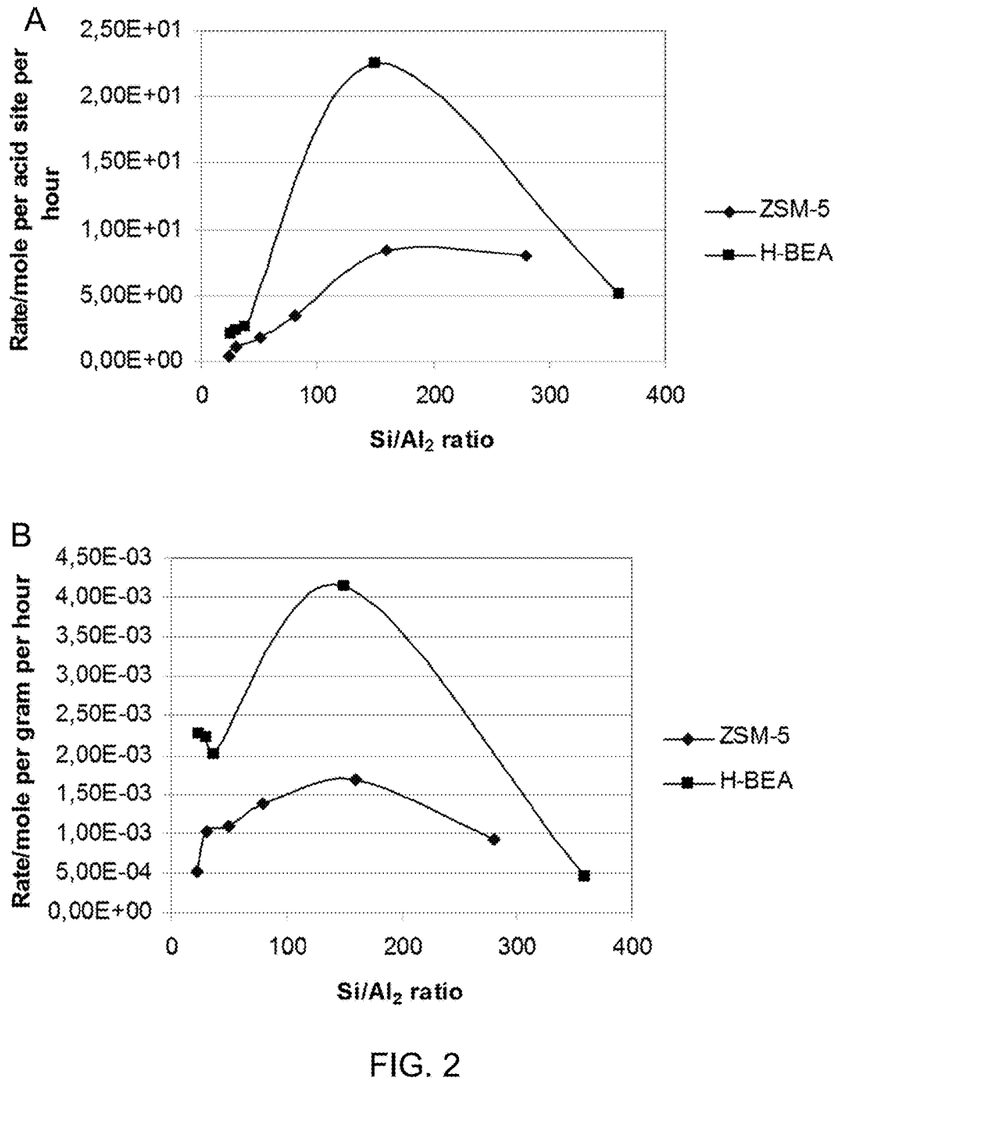

FIG. 2A shows the rate of lactide production per acid site (as calculated from the Si/Al$_2$ ratio) per hour for ZSM-5 and H-BEA zeolites, with varying Si/Al$_2$ ratios. For the all zeolites except H-BEA (150), the rate was calculated taking into account the amount of lactide formed after 3 hours. For the H-BEA zeolite with a Si/Al$_2$ ratio of 150 (H-BEA (150)), the rate was calculated taking into account the amount of lactide formed after 1.5 hours, because this catalyst proved to be significantly faster than the others. Taking this into account, it is clear that the H-BEA (150) zeolite provides the highest rate per acid site.

The rate of lactide formation per gram of zeolite is a suitable indicator for the suitability of the zeolites for the catalysis of lactide formation (or cyclic ester formation in general FIG. 2B shows the rate of lactide production per gram zeolite per hour for the same zeolites as in FIG. 2A. It is clear that although, for example, the ZSM-5 (160) zeolite provides a faster rate per acid site than the H-BEA (25) zeolite, the latter still provides a faster rate per gram of catalyst.

Degree of Polymerization

Via HPLC analysis of the reaction products, it was found that the average degree of polymerization (DP) of the formed oligomers using the zeolite catalysts was typically smaller than the DP of the formed oligomers using the reference catalysts (Amberlyst and sulfuric acid). Table 2 shows the reaction products and the average DP of the oligomers obtained with four different catalysts, under similar reaction conditions (oil bath of 130° C.; 3 h; 1 g L-LA 90 wt % (aqueous) in 10 mL toluene). The results indicate a much higher average DP of the oligomers using the Amberlyst and sulfuric acid catalysts, compared to the zeolite catalysts. This is an additional benefit of using zeolites as catalysts, byproduct formation is less pronounced and the average length of byproduct oligomers is very small, rendering them water soluble. Such small oligomers obtained with zeolite catalysts are more suitable for re-introduction in a further cycle, for instance via simple hydrolysis into lactic acid, than the longer oligomers obtained with the reference catalysts. Longer oligomers (DP>5-6) typically tend to part in the organic phase, which complicates the separation of the cyclic esters and the byproducts.

TABLE 2

| Catalyst | Amount of dry catalyst (g) | LA (%) | Lactide (%) | Oligomers (%) | DP |
|---|---|---|---|---|---|
| Sulfuric acid | 0.031 | 0.5 | 6.9 | 92.6 | 8.3 |
| Amberlyst 15 wet | 0.5 | 2 | 20.2 | 77.8 | 10 |
| H-BEA (Si/Al2 = 25) | 0.45 | 5.6 | 67.9 | 26.5 | 3.4 |
| ZSM-5 (Si/Al2 = 80) | 0.45 | 6.1 | 64.3 | 29.7 | 3.4 |
| ZSM-5 (Si/Al2 = 160) | 0.475 | 11.5 | 52.6 | 35.9 | 3.4 |

Regeneration of the Catalyst

The possibility to re-use the catalyst was assessed in a series of four identical runs with re-use of the catalyst. The reaction conditions were: oil bath of 130° C.; 7 h reaction time; 1.65 g 50 wt % L-LA (aqueous) in 10 ml toluene; 0.5 g H-BEA (Si/Al2=25). A Dean-Stark trap was used for removal of water from the reaction mixture. The same catalyst was re-used in the four successive runs. After the first run, the catalyst was re-used in the next run after filtration and drying at room temperature. This was repeated for the third run. After the third run, the catalyst was calcined in air at 450° C. for 12 hours, using a temperature ramp of 3° C. per minute. The results of the reactions are summarized in Table 3.

The results indicate that the re-use of the catalyst in runs 2 and 3 leads to a small decrease of the lactide formation. However, after calcination of the catalyst (run 4), a similar lactide formation is obtained as in the initial run 1. This shows that the catalyst may be fully regenerated via calcination.

TABLE 3

| Run | Lactide (%) | Oligomers (%) | Lactic acid (%) |
|---|---|---|---|
| 1 | 75.1 | 23.2 | 1.7 |
| 2 | 70.1 | 26.3 | 3.6 |
| 3 | 64.8 | 27.9 | 7.4 |
| 4 | 75.8 | 23.3 | 1.0 |

Influence of the Solvent

The influence of the solvent on the lactic acid yield was assessed in a series of reactions under identical conditions, except for the solvent. The reaction conditions are: 3 h reaction time; 1 g 90 wt % L-LA (aqueous) in 10 ml solvent; 0.5 g H-BEA (Si/Al2=25). The reaction was typically performed at the boiling point of the reaction mixture. A Dean-Stark trap was used for removal of water from the reaction mixture.

Figure 3:
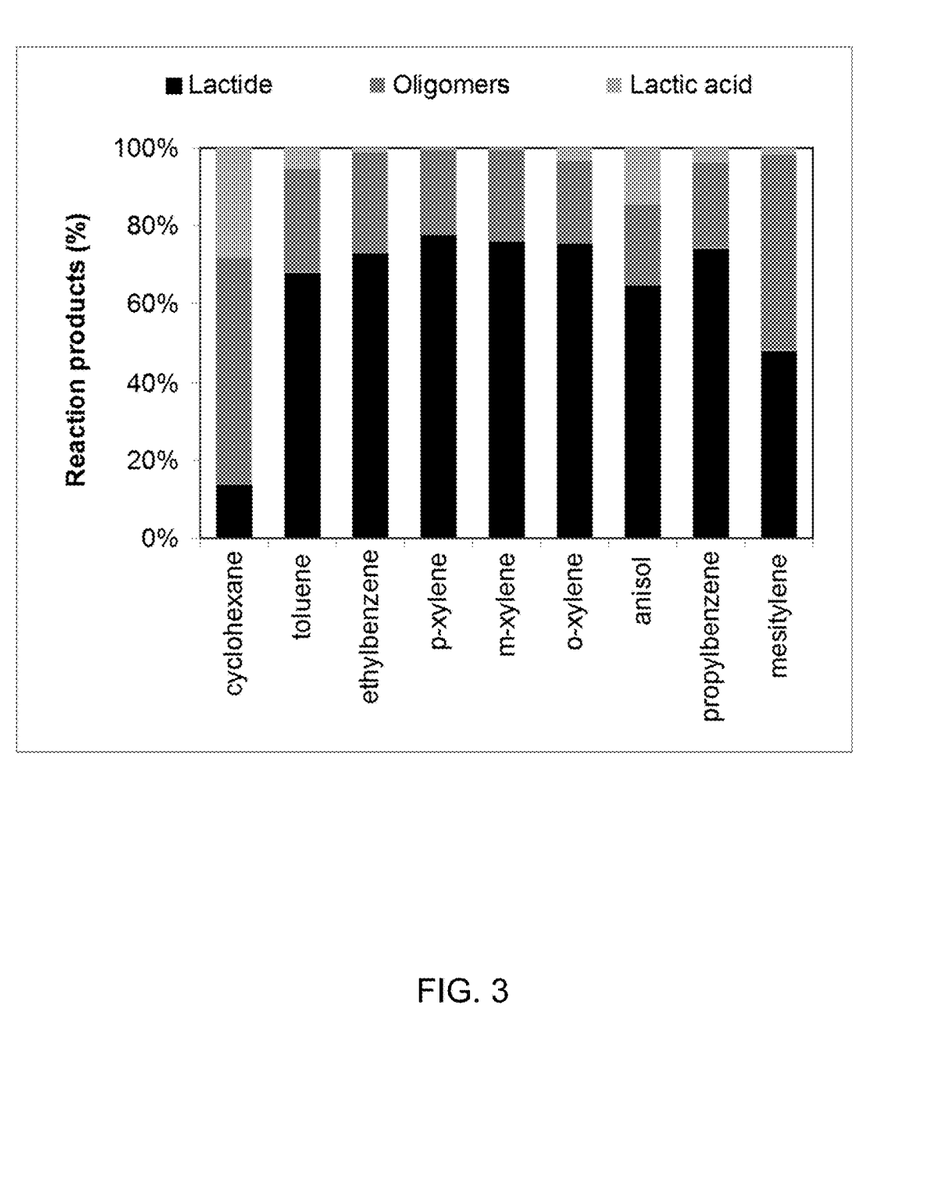
FIG. 3 Graph plotting the relative amounts of reaction products obtained with a H-BEA zeolite with a $Si/Al_2$ ratio of 25 for the synthesis of lactide, in various solvents.

The tested solvents (and their boiling points) were as follows: cyclohexane (81° C.), toluene (111° C.), ethylbenzene (136° C.), p-xylene (138° C.), m-xylene (139° C.), o-xylene (143° C.), anisol (154° C.), propylbenzene (158° C.), mesitylene (163° C.). The results of the reactions are plotted in FIG. 3. Accordingly, in some embodiments, suitable solvents at atmospheric pressure can be solvents allowing for a reaction temperature above 81° C. but below 163° C., under conditions of water removal.

Example 2: Preparation of Symmetric Cyclic Esters Other than Lactide 3,6-diethyl-1,4-dioxane-2,5-dione: (ethyl glycolide)
3,6-diethyl-1,4-dioxane-2,5-dione was prepared using 2-hydroxybutanoic acid (2-HBA) in 10 ml of o-xylene, in the presence of H-BEA, at an oil bath temperature of 170° C. A Dean-Stark trap was used for removal of water from the reaction mixture. The reactants and results are shown in Table 4, as determined by $^1$H-NMR and gas chromatography (GC).

TABLE 4

| Hydroxycarboxylic acid and amount | H-BEA | Reaction time | Cyclic ester | Yield (NMR) % | Yield (GC) % |
|---|---|---|---|---|---|
| Racemic 2-hydroxybutanoic acid 0.5 g | H-BEA (Si/Al$_2$: 25) 0.25 g | 3 h | R,S and meso | 45.4 | 46.9 |
| (R)-2-hydroxybutanoic acid 0.5 g | H-BEA (Si/Al$_2$: 25) 0.25 g | 1 h | R,R | 56.8 | nd |
| (S)-2-hydroxybutanoic acid 0.5 g | H-BEA (Si/Al$_2$: 150) 0.25 g | 1 h | S,S | 75.5 | 77.6 | nd: not determined

Figure 4:
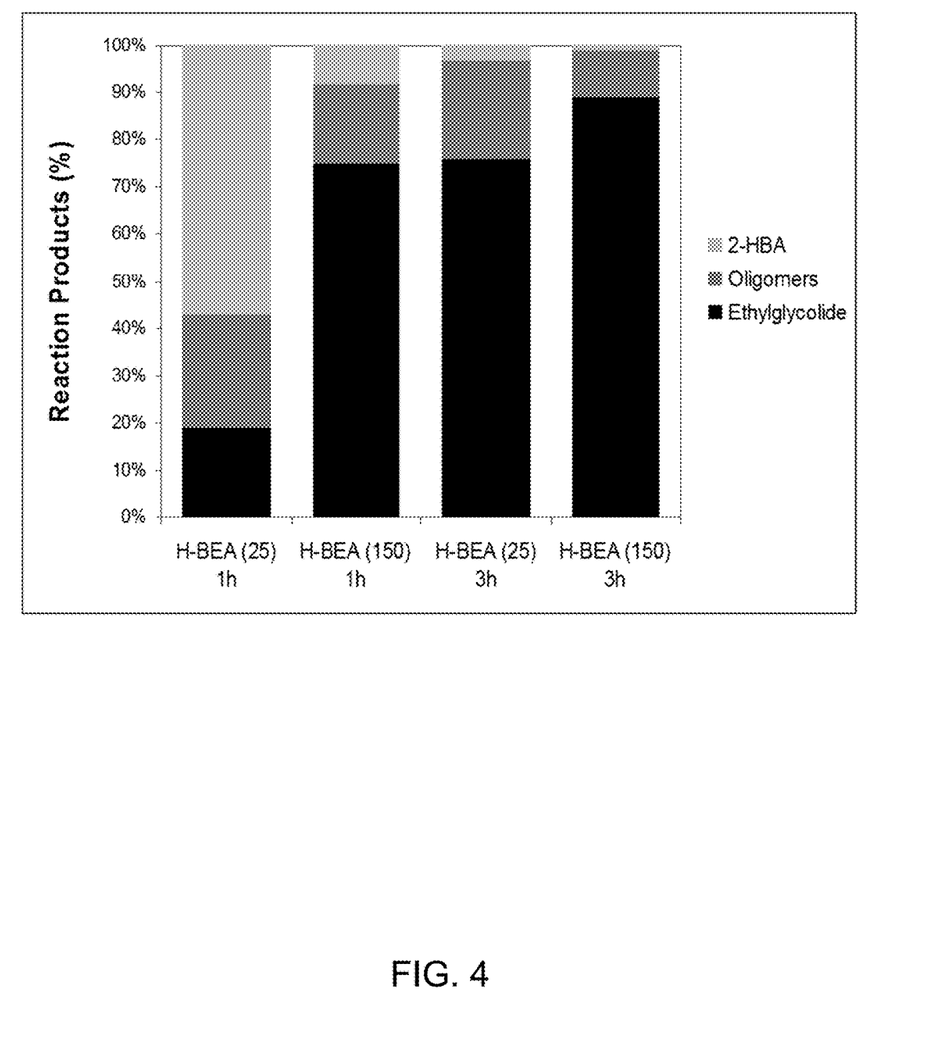
FIG. 4 Graph plotting the relative amounts of reaction products obtained with H-BEA zeolites with $Si/Al_2$ ratios of 25 and 150 for the synthesis of ethyl glycolide from 2-hydroxybutanoic acid.

The results indicate that H-BEA is a suitable catalyst for the production of racemic or enantiomerically pure ethyl glycolide. The zeolite with a Si/Al$_2$ ratio of 150 appears to be faster and more selective. This was confirmed in further experiments, wherein H-BEA with Si/Al$_2$ ratios of 25 and 150 were tested for the production of R,R-ethyl glycolide (FIG. 4; Reaction conditions: 0.5 g (R)-2-HBA, 0.25 g H-BEA; 10 mL o-xylene; oil bath temperature of 170° C.; reaction time 1 h or 3 h).

The produced ethyl glycolide could then be used to prepare poly(ethyl glycolide) by ring opening polymerization (as described in Yin et al. (1999). Macromolecules, 32(23), 7711-7718) in the presence of tin-2-octanoate/neopentylalcohol (ratio catalyst:initiator 1:1), the ratio monomer:catalyst was 100:1. The polymerization was performed at 130° C. under light pressure of helium for 2.5 hour. After 2.5 h of reaction a polymer of about 3000 g/mol was obtained.

3,6,-divinyl-1,4-dioxane-2,5-dione 3,6-divinyl-1,4-dioxane-2,5-dione was prepared using 0.5 g (DL)2-hydroxy-3-butenoic acid in 10 ml of toluene, in the presence of H-BEA (Si/Al$_2$:25) (0.25 g) at an oil bath temperature of 130° C. A Dean-Stark trap was used for removal of water from the reaction mixture. After 24 h of reaction, the yield was 24%.

3,6-dibutyl-1,4-dioxane-2,5-dione 3,6-dibutyl-1,4-dioxane-2,5-dione was prepared using 2-hydroxyhexanoic acid (0.5 g) in 10 ml of o-xylene, in the presence of H-BEA (Si/Al$_2$:25) (0.25 g), at an oil bath temperature of 170° C. A Dean-Stark trap was used for removal of water from the reaction mixture. After 3 h of reaction, the yield was 9.5% as measured by NMR.

1,4-dioxane-2,5-dione (glycolide)

Glycolide was prepared using 70 wt % glycolic acid (aqueous) (1 g) in 10 ml of toluene, in the presence of ZSM-5 (Si/Al$_2$:160) (0.5 g), using an oil bath at a temperature of 170° C. A Dean-Stark trap was used for removal of water from the reaction mixture. After 3 h of reaction, the yield was 31.1%.

Example 3: Preparation of Asymmetric Cyclic Esters

Equimolar amounts of D-2-hydroxybutyric acid and L-lactic acid were mixed in o-xylene and reacted in the presence of H-BEA (Si/Al$_2$:25) (0.25 g) at an oil bath temperature of 170° C. A Dean-Stark trap was used for removal of water from the reaction mixture. After 3 h of reaction, the products as listed in Table 5 were obtained, as measured by H$^1$-NMR and confirmed by GC.

TABLE 5

| Cyclic ester | Yield GC (%) | Yield NMR (%) |
| --- | --- | --- |
| L-L-lactide | 29 | 22 |
| D-D-ethyl glycolide | 23.8 | 21.5 |
| Asymmetric meso cyclic ester | 46.5 | 42 |

Example 4: Caprolactone

Caprolactone was prepared using 6-hydroxyhexanoic acid (0.5 g) in 10 ml of toluene, in the presence of H-BEA (Si/Al$_2$:25) (0.2 g), using an oil bath at a temperature of 130° C. A Dean-Stark trap was used for removal of water from the reaction mixture. After 3 h of reaction, the yield was 99% as measured by GC.

Example 5: Caprolactam

Caprolactam was prepared using 6-aminohexanoic acid (1 g) in 10 ml of toluene, in the presence of H-BEA (Si/Al$_2$:25) (0.5 g), using an oil bath at a temperature of 130° C. A Dean-Stark trap was used for removal of water from the reaction mixture. After 3 h of reaction, the yield was 5%.

The invention claimed is:

1. A process for preparing a compound, comprising:
   contacting at least one amino-carboxylic acid; or an ester, or salt thereof; and wherein said amino carboxylic acid is a 2-amino-carboxylic acid having the formula (Ib):

(Ib)

wherein R$^1$ and R$^2$ are each independently hydrogen or a group selected from a C$_{1-6}$ alkyl; a C$_{2-6}$ alkenyl; a C$_{6-}$10 aryl; a C$_{1-10}$ alkylC$_{6-}$10arylene; a C$_{6-10}$arylC$_{1-6}$alkylene; or C$_{2-6}$alkynyl; each group being optionally substituted by one or more substituents selected from C$_{1-6}$alkyl, a C$_{1-6}$alkyloxy;

or a 6-amino-carboxylic acid, wherein the 6-amino-carboxylic acid is a 6-aminohexanoic acid, optionally substituted with one or more groups selected from the group consisting of a halogen, a C$_{1-4}$alkyl, a C$_{2-4}$alkenyl, or a C$_{2-4}$alkynyl;

with at least one acidic zeolite comprising:
   two or three interconnected and non-parallel channel systems, wherein at least one of said channel systems comprises 10-or more-membered ring channels; and a framework Si/X$_2$ ratio of at least 24 as measured by NMR; or
   three interconnected and non-parallel channel systems, wherein at least two of said channel systems comprise 10-or more-membered ring channels; and a framework Si/X$_2$ ratio of at least 8 as measured by NMR;
wherein each X is Al or B, wherein the process is performed at a pressure between 0.5 and 20 bar, and wherein said compound is a cyclic amide of formula (II):

(II)

wherein Z$^1$ is NH, wherein Z$^2$ is NH; and
wherein R$^1$ and R$^2$ are each independently hydrogen or a group selected from C$_{1-6}$ alkyl; C$_{2-6}$ alkenyl; C$_{6-10}$ aryl; C$_{1-10}$ alkylC$_{6-10}$arylene; C$_{6-10}$arylC$_{1-6}$alkylene; or C$_{2-6}$alkynyl; each group being optionally substituted by one or more substituents selected from C$_{1-6}$alkyl, C$_{1-6}$alkyloxy.

2. The process according to claim 1, wherein at least one of said interconnected and non-parallel channel systems comprises 12-or more membered ring channels.

3. The process according to claim 1, wherein said zeolite has a Brønsted acid density between 0.05 and 6.5 mmol/g dry weight.

4. The process according to claim 1, wherein said zeolite comprises a BEA topology, a MFI topology, a FAU topology, a MEL topology, a FER topology, and a MWW topology.

5. The process according to claim 1, wherein said zeolite comprises a BEA topology.

6. The process according to claim 1, wherein X is Al.

7. The process according to claim 1, wherein said zeolite comprises at least three interconnecting and non-parallel channel systems.

8. The process according to claim 1, wherein said aminocarboxylic acid is provided in a composition comprising said amino-carboxylic acid in a concentration of at least 1 wt % in a solvent based on a total weight of the composition.

9. The process according to claim 1, wherein said process is performed under conditions of water removal.

10. The process according to claim 9, wherein said water removal is performed via azeotropic distillation.

* * * * *